(12) United States Patent
Trudil

(10) Patent No.: US 6,395,504 B1
(45) Date of Patent: May 28, 2002

(54) USE OF PHAGE ASSOCIATED LYTIC ENZYMES FOR THE RAPID DETECTION OF BACTERIAL CONTAMINANTS

(75) Inventor: David Trudil, Reisterstown, MD (US)

(73) Assignee: New Horizons Diagnostics Corp., Columbia, MD (US)

( * ) Notice: Subject to any disclaimer, the term of this patent is extended or adjusted under 35 U.S.C. 154(b) by 83 days.

(21) Appl. No.: 09/654,484

(22) Filed: Sep. 1, 2000

(51) Int. Cl.[7] .............................. C12Q 1/02; C12Q 1/04; C12Q 1/06; C12Q 1/00; C12M 1/34
(52) U.S. Cl. ............................ 435/29; 435/34; 435/39; 435/4; 435/18; 435/23; 435/287.1; 435/287.3; 435/287.4; 435/288.7; 435/8; 422/55
(58) Field of Search .......................... 435/29, 34, 39, 435/4, 18, 23, 287.1, 287.3, 287.4, 288.7, 8; 422/55

(56) References Cited

U.S. PATENT DOCUMENTS

| | | | |
|---|---|---|---|
| 3,983,209 A | 9/1976 | Schmitt | 424/94 |
| 4,062,941 A | 12/1977 | Davies | 424/94 |
| 4,122,158 A | 10/1978 | Schmitt | 424/94 |
| 4,885,163 A | 12/1989 | Shaar et al. | 514/2 |
| 4,957,686 A | 9/1990 | Norris | 424/94.1 |
| 5,162,226 A | 11/1992 | Beachey et al. | 424/94.1 |
| 5,604,109 A | 2/1997 | Fischetti et al. | 424/94.1 |
| 5,688,501 A | 11/1997 | Merril et al. | 424/94.1 |
| 5,741,487 A | 4/1998 | Asai et al. | 514/2 |
| 5,833,924 A * | 11/1998 | McClintock et al. | 422/52 |
| 5,882,631 A | 3/1999 | Suga et al. | 514/2 |
| 5,985,271 A | 11/1999 | Fischetti et al. | 424/94.1 |
| 5,997,862 A | 12/1999 | Fischetti et al. | 424/94.1 |
| 6,017,528 A | 1/2000 | Fischetti et al. | 424/94.1 |
| 6,056,954 A | 5/2000 | Fischetti et al. | 424/94.1 |
| 6,056,955 A | 5/2000 | Fischetti et al. | 424/94.1 |
| 6,113,887 A | 9/2000 | Mori et al. | 424/54 |
| 6,132,970 A | 10/2000 | Stemmer | 435/6 |
| 6,177,554 B1 | 1/2001 | Woo et al. | 435/29 |
| 6,187,757 B1 | 2/2001 | Clarkson et al. | 435/29 |
| 6,238,611 B1 | 5/2001 | Fischetti et al. | 424/94.1 |
| 6,248,324 B1 | 6/2001 | Fischetti et al. | 424/94.1 |
| 6,254,866 B1 | 7/2001 | Fischetti et al. | 424/94.1 |
| 6,264,945 B1 | 7/2001 | Fischetti et al. | 424/94.1 |
| 6,277,399 B1 | 8/2001 | Fischetti et al. | 424/94.1 |
| 6,326,002 B1 | 12/2001 | Fischetti et al. | 424/94.1 |
| 6,335,012 B1 | 1/2002 | Fischetti et al. | 424/94.1 |

FOREIGN PATENT DOCUMENTS

| | | |
|---|---|---|
| EP | 0 510 907 A | 10/1992 |
| WO | WO 96 07329 A | 3/1996 |
| WO | WO 97 02351 A | 1/1997 |
| WO | WO 99 04809 A | 2/1999 |

OTHER PUBLICATIONS

Reisenger, et al. (1998) "Characterization of *Escherichia coli* lysis using a family of chimeric E–L Genes" *Fems Microbiol Letter.* 164(1) p. 159–167.

(List continued on next page.)

*Primary Examiner*—Louise N. Leary
(74) *Attorney, Agent, or Firm*—Jonathan Grant; Grant Patent Services

(57) ABSTRACT

A method for the use of a phage associated lysing enzyme for the detecting the presence and determining the quantity of bacteria present in or on a wide variety of substances is described. The total concentration of microbes is determined by adding or incorporating a phage associated lytic agent to a disposable test system device with the luminescent reagents luciferin and luciferase, and introducing the disposable test system into a luminometer that can read the luminescence. Other systems can be used with the lytic enzymes for the quantitative and qualitative determination for the presence of bacteria.

38 Claims, 4 Drawing Sheets

OTHER PUBLICATIONS

Sheehan MM, et al. (1997) "The lytic enzyme of the Pneumococcal Phage Dp–1: a chimeric lysis of intergeneric origin." *Mol. Microbiol.* 25(4) p. 717–725.

Young et al. (2000) "Phages will out: strageggies of host cell lysis." *Trends in Microbiology.* 8(4) p. 120–127.

Garcia et al.(1997) "The Pneumococcal cell wall degrading enzymes: A modular design to create new lysins"? *Microb. Drug Resist.* 3(2): p. 199–211.

Sheehan MM, et al., (1997) "The Lytic Enzyme of the Pneumococcal Phage Dp–1: a Chimeric Lysin of Intergeneric Origin" *Mol. Microbiol.* 25(4) p. 717–25.

Garcia P, et al. (1997) "Bacteriophages of Streptococcus Pneumoniae: a molecular approach" *Microb. Drug Resist.* 3(20) 165–76.

Sheehan, MM, et al.(1996) "Analysis of the catalytic domain of the lysin of the lactococcal bacteriophage Tuc2009 by chimeric gene assembling." *FEMS Microbiol. Lett.* 14(1): p. 23–28.

Sanz, JM, et al. (1996) "Construction of a multifunctional pneumococcal murein hydrolase by module assembly." *Eur. J. Biochem.* 235(3):601–5.

Lopez R, et al. (1995) "Architecture and Domain Interchange of the Pneumococcal Cell Wall Lytic Enzymes" *Dev. Biol. Stand.* 85 p. 273–81.

Croux, et al. (1993) "Interchange of Functional Domains Switches Enzymes Specificity: Construction of a chimeric pneumococcal–clostridial cell wall lytic enzyme." *Mol. Microbiology.* 9(5) p. 1019–25.

Diaz, E. et al.(1990) Chimeric phage–bacterial enzymes: a clue to the modular evolution of genes. *PNAS.*87(20) p. 8125–9.

Diaz, E. et al.(1990) "Chimeric pneumoccal cell wall lytic enzymes reveal important physiological and evolutionary traits." *J. Biol. Chem.*266(9) p. 5464–71.

Lopez, et al. (1997) "The pneumococcal cell wall degrading enzymes: A modular design to create new lysins?" *Microbiological Drug Resistance.* 3(2) p. 199–211.

Loessner, et al. (1999) "Evidence for a holin–like protein gene fully embedded out of frame in the endolysin gene of *Staphylococcus aureus* Bacteriophage." (1999) *Journal of Bacteriology.* 181(15) p. 4452–4460.

Witte, A et al. (1998) "Characterization of *Escherichia coli* lysis using a family of chimeric E–L genes." *FEMS Microbiol. Lett.*, 164(1), p. 159–167.

Martin, Ana C et al (1998): "Functional analysis of the two–gene lysis system of the pneumococcal phage Cp–1 in homologous and heterologous host cells." *Journal of Microbiology* 180(2), p. 210–217.

Oki Masaya et al. (1997) "Functional and structural features of the holin HOL protein of the Lactobacillus plantarum phage phi–gle: Analysis in *Escherichia coli* system." *Gene* (AMSTERDAM) 197(1–2) p. 137–145.

Young, Ry et al. (2000) "Phages will out: strategies of host cell lysis."*Trends in Microbiology,* 8(3) p. 120–127.

Nelson, et al. (2001) "Prevention and elimination of upper respiratory colonization of mice by Group A Streptococci by using a bacteriophage lytic enzyme." *PNAS.* 98 (7) p. 4107–4112.

Garcia, et al. (1987) "Purification and biochemical characterization of the pneumococcal bacteriophage Cp–1 lysin." *Journal of Virology* 61 (8) p. 2573–2580.

Loessner, et al. (1996) "Modified Listeria bacteriophage lysin genes (ply) allow efficient overexpression and one–step purification of biochemically active fusion proteins." *Applied and Environmental Microbiology.* 62(8) p. 3057–3060.

\* cited by examiner

USE OF PHAGE ASSOCIATED LYTIC ENZYMES FOR THE RAPID DETECTION OF BACTERIAL CONTAMINANTS

FIELD OF THE INVENTION

The present invention relates to a method for the use of a phage associated lysing enzyme for the detecting the presence and determining the quantity of bacteria present in or on a wide variety of substances.

BACKGROUND OF THE INVENTION

Microbial contamination of surfaces and substances is a significant cause of morbidity and mortality. Rapid and routine procedures for quantitative determination of bacteria present on surfaces is frequently of vital importance, particularly in food processing, drinking water, and in hospitals. Food poisoning is often a result of microbial contamination of meat or food that occurs during processing. Contamination can be spread through contact of food with surfaces. In addition, spread of disease in hospitals and other facilities often occurs as a result of passage of infectious microbes on the surface of clothes or equipment.

A key feature of these applications is the requirement for rapid testing within minutes, a method that will overcome the potential contaminants from a variety of surfaces, a requirement for no cross-over in the results from one test to a second, and a need for both general and specific testing for microbes, that is, the ability to test for contamination by both microbial counts and the ability to test for the presence of specific microbes.

Various methods have been utilized to measure microbial contamination on surfaces. Traditional procedures for assaying bacteria on surfaces are based on swabbing the surface followed by a culture of the swab for 24 to 48 hours in or on media that supports the growth of microbial species. The cultures are observed manually or with automated instrumentation to determine the number of colonies that have formed as an indicator of the number of microbes initially present on the surface. The disadvantages of this methodology are long assay times, requirements for specially trained personnel, and possible inadequate identification of the presence of certain potentially pathogenic microbes whose growth is not supported by the specific media or environment. In particular, it may be difficult to detect fungal contamination by this method. In addition, in many of the potential applications, the method does not give results in the time frame required for effective response.

Luminescent reactions have been utilized in various forms to detect bacteria in fluids and in processed materials. In particular, bioluminescent reactions based on the reaction of adenosine triphosphate (ATP) with luciferin in the presence of the enzyme luciferase to produce light (the "firefly" reaction) have been utilized. Since ATP is present in all living cells including all microbial cells, this method can be used in a rapid assay to obtain a quantitative estimate of the number of living cells in a sample. Early discourses on the nature of the reaction, the history of its discovery, and its general area of applicability are provided by E. N. Harvey (1957), A History of Luminescence: From the Earliest Times Until 1900, Amer. Phil. Soc., Philadelphia Pa and W. D. McElroy and B. L. Strehler (1949) Arch. Biochem. Biophys. 22:420–433. Alternatively, chemiluminescent detection by isoluminol or similar compounds has been used. This method is based on the detection of iron-containing substances in microbes.

Test procedures exemplifying the use of bioluminescent reactions for bacterial determinations and, specialized instrumentation for measurement of the associated light emission, are known and have been disclosed. Plakas (U.S. Pat. Nos. 4,013,418, 4,144,134, and 4,283,490) teaches a bioluminescent assay for the detection of bacteria in a sample including the steps of lysing non-bacterial cells, effecting filtration by positive pressure, washing, lysing bacterial cells and detecting ATP released with a luciferin/luciferase/Mg2+ regent. The art in this patent does not deal with the specific problems associated with collection of material from a surface or with the detection of specific bacteria. No issue of the timing is mentioned and the invention as disclosed would require significant time.

Chappelle in U.S. Pat. No. 4,385,112 discloses a method for detection of bacteria in water based on bioluminescence. This test requires several hours to perform and is specifically addressed to the detection of total bacterial content in water.

Miller (PCT application U.S. Ser. No. 88/00852) discusses a similar assay for use with urine samples, but does not discuss the issues of collection from a surface and the assay timing is not specifically set forward in this application. further, no method for detection of specific bacteria is elucidated.

U.S. Pat. No. 3,933,592 (Clendenning) discusses a method for bioluminescent detection of microbial contamination and in the examples refers to performing the procedure in less than 2 minutes. The procedure does not involve pre-treatment phases and the removal of somatic cell ATP.

U.S. Pat. No. 5,258,285 (Aegates) discloses a method for detection of bacterial concentration in a sample that utilizes a filtration step, a washing step to remove extraneous material including somatic cell ATP, establishing an extraction chamber in which luciferin/luciferase/Mg2+ is added and the reaction measured. This method does not mention time. In addition, it utilizes separate chambers for washing, extracting the bacterial ATP, and measuring the reaction. This may potentially result in decreased sensitivity due to loss of the material in the process of transferring the solution from chamber to chamber. Further, the method does not describe a means of collecting a sample from a surface.

U.S. Pat. No. 5,736,351 (Miller et al) discloses a method and device for determining the presence and concentration of total microbial contamination or the presence and concentration of a specific microbial species on a surface is described. The method consists of a means of a collection device and fluid for removing the microbes from the surface and suspending them in a fluid phase. An aliquot of the fluid phase is introduced into a disposable test ticket which allows filtration of the sample to remove extraneous substances including somatic cells, and concentration of the microbes. The total concentration of microbes is determined by adding a somatic and bacterial releasing reagent to a disposable test device which comprises a membrane containing the luminescent reagents luciferin and luciferase, and introducing the disposable test device into a luminometer that can read the luminescence from the underside.

SUMMARY OF THE INVENTION

The present invention is a method and device for detecting the presence and/or concentration of specific bacteria found on surfaces, in or on food, in the air, water, or in biological samples, by the use of bioluminescence. This device and method relies on the use of at least one lytic enzyme produced by a bacteria infected with a bacteriophage specific for the bacteria to lyse the bacteria, allowing for the release of ATP in the bacteria and its detection by chemical-bioluminescence analysis. Unlike the method and device of U.S. Pat. No. 5,5736,351, the lytic enzyme can be used in place of the bacterial releasing agent, and it may not even be necessary to use the somatic releasing agent, thereby simplifying the procedures.

Reports have described the characteristics of an enzyme produced by the group C streptococcal organism after being infected with a particular bacteriophage identified as C1 (Maxted, W. R. "The Active Agent in Nascent Page Lysis of Streptococci," J. Gen Micro., vol 16, pp 585–595, 1957, Krause, R. M., "Studies on the Bacteriophages of Hemolytic Streptococci," J. Exp. Med, vol. 108, pp 803–821, 1958) and Fischetti, (Fischetti, V. A., et al, "Purification and Physical Properties of Group C Streptococcal Phage Associated Lysin," J. Exp. Med, Vol 133 pp. 1105–1117, 1971). The enzyme was given the name lysin and was found to specifically cleave the cell wall of group A, group C, and group E streptococci. These investigators provided information on the characteristics and activities of this enzyme with regard to lysing the group A streptococci and releasing the cell wall carbohydrate.

U.S. Pat. No. 5,604,109 (Fischetti et al.)(which is incorporated herein in its entirety by reference) teaches the rapid and sensitive detection of group A streptococcal antigens by a diagnostic test kit which utilizes a sampling device consisting of a throat swab made of synthetic or natural fibers such as Dacron or rayon and some type of shaft which holds the fibers and which is long enough to place the fibers in the tonsillar area and capable of being used to swab the area to remove sufficient numbers of colonizing or infecting organisms. The swab can then be placed in the enzyme extraction reagent in several configurations and subsequently used in an immunoassay. The invention can comprise a test kit for detecting Group A streptococci antigens, comprising an extraction reagent containing lysin enzyme for releasing Group A streptococcal components, and a ligand capable of binding with a component of the Group A streptococcus.

U.S. Pat. No. 5,997,862 (Fischetti, et. al.) and U.S. Pat. No. 5,985,271 (Fischettietal.) disclose the use of an oral delivery mode, such as a candy, chewing gum, lozenge, troche, tablet, a powder, an aerosol, a liquid or a liquid spray, containing a lysin enzyme produced by group C streptococcal bacteria infected with a C1 bacteriophage for the prophylactic and therapeutic treatment of Streptococcal A throat infections, commonly known as strep throat.

U. S. patent application Ser. No. 395,636 (Fischetti, et. al) discloses a method for the prophylactic and therapeutic treatment of bacterial infections which comprises the treatment of an individual with an effective amount of a lytic enzyme composition specific for the infecting bacteria, and a carrier for delivering said lytic enzyme. The methods disclosed included the topical, oral, and respiratory methods of delivering the enzyme. Another method disclosed in that application includes the use of suppositories. These methods and compositions can be used for the treatment of upper respiratory infections, skin infections, wounds, and burns, vaginal infections, eye infections, intestinal disorders and dental problems.

U.S. patent application Ser. No. 395,637 (Fischetti et al.) discloses a method and composition for the topical treatment of streptococcal infections by the use of a lysin enzyme blended with a carrier suitable for topical application to dermal tissues. The method for the treatment of dermatological streptococcal infections comprises administering a composition comprising an effective amount of a therapeutic agent, with the therapeutic agent comprising a lysin enzyme produced by group C streptococcal bacteria infected with a C1 bacteriophage. The therapeutic agent can be in a pharmaceutically acceptable carrier.

In one embodiment of the present invention, the method comprises first collecting a sample in a prescribed fashion using a collection apparatus means comprised of an absorbent or adsorbent material. The collection apparatus means is placed into a container containing a fluid and agitated to release the surface contaminants from the collection apparatus means into the fluid. The collection apparatus means can be in the form of a sponge or a swab and the container can be a bag, tube, or small cup. An aliquot of the fluid phase is subsequently transferred to a disposable test device comprised of a translucent hollow cylinder, open on the top and having a porous filter attached on the bottom. The fluid phase is filtered through the disposable test device comprised of a translucent hollow cylinder, open on to and having a porous filter attached on the bottom. The fluid phase is filtered through the disposable test device by applying either positive or negative pressure resulting in retention of microbes or target analytes on the surface of the filter. The filtration process results in the concentration of an analyte and the removal of any interfering substances from the collectate prior to testing, such as inhibitors or any nonspecific materials to maximize test sensitivity and specificity. The filter retentate can be washed by adding appropriate wash solution and reapplying appropriate pressure to force the fluid phase through the filter. Another feature of the present invention is that the retentate captured on the filter of the disposable test device can be assayed by a chemiluminescent or bioluminescent test method. This final step of the test method comprises adding a luminescent substrate to the retentate resulting in a chemiluminescent reaction and measuring the light output from said chemiluminescent reaction by using a photometer that accommodates the disposable device in a manner which allows its precise and reproducible positioning with respect to the surface of the photosensor and which precludes any possible loss of the final reaction mixture during and after the measurement cycle.

During this procedure, somatic releasing agent may be added to the cells as they are collected on the filter. The filter is washed. Then, 10 to 15 seconds prior to the chemiluminescent reaction, at least one lytic enzyme produced by a bacteria infected with a bacteriophage specific for that bacteria is applied to the filter.

The present invention allows for a surface contaminant to be identified and/or concentration determined in less than 1 hour from time of collection to end result, and generally in less than 15 minutes.

More specifically, the present invention comprises a method for performing chemiluminescent assays such as bioluminescent assays for ATP, including those utilizing, enhancers, or enzymes such as adenylate kinase, chemiluminescent immunoassay, reflectance, conductive or DNA probe assays. One embodiment of the present invention is a method for determining the microbial contamination by a specific bacteria comprising the steps of:

a) collecting a surface sample with a collection means;

b) agitating said collection apparatus means with a fluid phase to dislodge the surface contaminants into a fluid phase, said fluid phase becoming the collectate;

c) placing an aliquot of said collectate into a disposable test device;

d) applying a positive pressure to the top of the disposable test device or negative pressure to the bottom of the disposable test device to eliminate the liquid phase containing free ATP and any chemical inhibitors as well as concentrating the bacteria at the interface;

e) adding at least one lytic enzyme produced by a bacteria infected with a bacteriophage specific for the bacteria; that lyses the specific bacterial cells present in the aliquot;

f) adding ATP free luciferin and luciferase reagent, and g) determining the amount of ATP present by measuring the light emitted through translucent sides of said disposable test device.

The step of adding a washing/lysing reagent that lyses any somatic cells present in the aliquot may be included prior to applying the positive pressure to the top of the disposable test device or negative pressure to the bottom of the disposable test device.

The choice of collection fluids are well known to those skilled in the art. Generally the fluid is comprised of a detergent, salt, or buffer or any combination thereof that maintains the integrity of the microbial cell walls. A fluid consisting of 0.15M sodium chloride containing 0.5% Tween 20 detergent is one such choice. It is possible to use other formulations including phosphate or HEPES buffered saline and other detergents including zwitterionic detergents and non-ionic detergents.

It will be obvious to a person skilled in the art that mixing of reactant could be achieved in any of the steps through the use of a micropipette. The detection method of this invention specifically allows for both the concentration of analyte and any resulting chemiluminescent reaction caused by the presence of said analyte to occur within the chamber of the disposable test device. An added feature of the disposable test device is that the diameter of the filter is from 0.5 to 5.0 cm, preferably about 1.0 cm, so that the volume of bioluminescent or chemiluminescent substrate solution is minimized to maximize signal output to the photodetector means. The final volume of the substrate should be between 20 $\mu$l to 1000 $\mu$l, most preferably about 60 $\mu$l to 100 $\mu$l. The disposable test device can be inserted into a complementary device comprising a larger (liquid tight) at least two component chamber that can house the disposable test device and through which a volume of collectate greater than 500 $\mu$l can pass through the filter under positive or negative pressure and retain the microbes or the analytes of interest onto the surface of the filter. For example, the disposable test device can be inserted into the lower chamber of the two component device, said lower chamber having an outflow for the filtrate to which is attached a removable upper chamber of the two component device. The upper chamber comprising a liquid tight seal to said lower compartment and having an intake valve. Said intake valve can be configured for a complementary Luer tip fitting for attachment of a Luer tipped syringe. Said syringe may include at least one series of prefilter(s) to remove any larger debris from entering the filter of the disposable test device. At completion of passing the collectate through the filter of the disposable test device, the two component device can be opened, and the disposable test device physically removed. Said disposable test device now containing the retentate from a large volume of collectate (i.e. 50 ml). The filtration of said large volume of collectate enables increased sensitivity for analyte detection of the collectate fluid. Said disposable test device is then processed as previously described.

The luciferin/luciferase chemiluminescent reactions for ATP are well known. Other chemiluminescent reactions employing bacterial luciferase reactions, or luminols for total microbial determinations can be easily adapted to the methods and devices of the present invention.

The luciferin/luciferase chemiluminescent reactions for ATP are well known. Other chemiluminescent reactions employing bacterial luciferase reactions, or luminols for total microbial determinations can be easily adapted to the methods and devices of the present invention.

The invention further concerns a detection method in which the presence and quantity of specific microbes on a surface can be detected in a time frame less than one hour, said method comprising the steps of a) Providing a clean disposable test device comprising an open top, translucent sides and a porous filter attached to the bottom side, b) Adding an aliquot of collectate, said collectate being that described as above, c) Adding an appropriate wash solution comprised of detergent, or buffered salts or a combination thereof, d) Applying positive pressure to the top of the disposable test device, or negative pressure to the bottom of the disposable test device to remove fluid from the device and deposit microbes or target analytes directly or indirectly onto the surface of the porous filter, e) Adding a specific lytic enzyme directed against the specific microbes to be detected;

f) Adding a chemiluminescent substrate and determining the amount of light emitted by the chemiluminescent substrate using a photometer that accommodates the disposable test device in a manner which allows its precise positioning with respect to the surface of the photosensor and which precludes any possible loss of the final reaction mixture during and after the measurement cycle.

In yet another embodiment of the invention, all of the chemicals and solutions (except for the somatic cell releasing agent and the lytic enzyme) are in a disposable membrane ticket. Such a device is easier to use, particularly in the field, than the use of a disposable test device or large volume concentration device. Fewer liquids need to be added to the membrane ticket, allowing for ease of use, less spillage, a more mobile system and more accurate results. Virtually all of the elements of the invention are essentially self contained in the disposable filter trap.

In yet another embodiment of the invention, all of the chemicals and solutions including the somatic cell releasing agent and the lytic enzyme, are included in the disposable membrane ticket.

The membrane ticket preferably comprises a hinged two sided plastic, cardboard, or paper support having a top and bottom section, and an absorbent pad or disk positioned on top of the inner side of the top section. On top of the absorbent disk is a glass filter membrane, which may be held in place by a plastic or paper rigid layer.

In another embodiment of the invention, the method is used to test bacteria in air samples.

In yet another embodiment of the invention, the method is used to test bacterial contamination of body fluids.

In yet another embodiment of the invention, the method is used to test bacterial contamination of potable water.

In another embodiment of the invention, the method is used to test bacterial contamination of food stuffs.

The bottom section of the membrane ticket preferably comprises a transparent window on the outer side of the bottom section, and a luciferin-luciferase immobilized on the membrane.

Various buffers for extracting antigens and washing immune complexes are well known to those skilled in the art.

DETAILED DESCRIPTION OF THE PREFERRED EMBODIMENT

Figure 1:
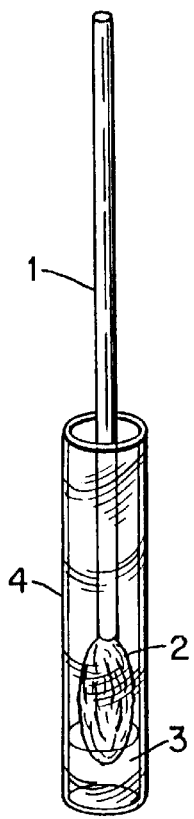
FIG. 1 is a side view of the collection apparatus means comprising a shaft, absorbent tip, and a container with fluid.

FIG. 1 is a drawing of a collection apparatus means comprised of a shaft 1 and absorbent tip 2. The absorbent tip 2 is wetted with an excess of collection fluid 3 and used to wipe a circumscribed area of a surface to be monitored. After wiping the area, the absorbent tip 2 is placed into a container 4 and agitated to release any of the absorbed bacteria into the collection fluid 3.

Figure 2:
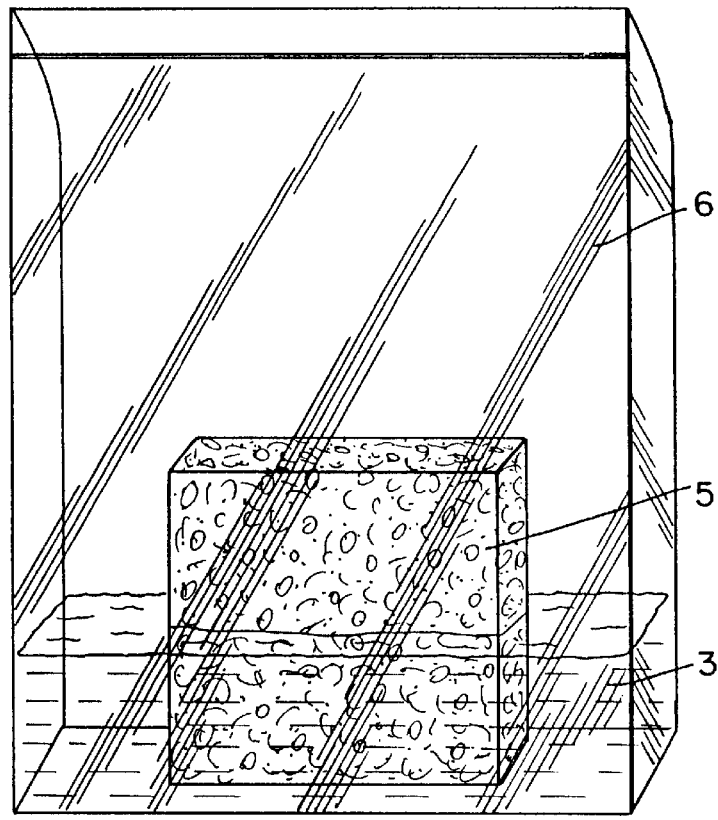
FIG. 2 is an angular side view of the collection apparatus means comprising a sponge and a bag with fluid.

As shown in FIG. 2 the collection apparatus means may be comprised of a sponge 5. The sponge 5 is wetted with collection fluid 3 and used to wipe a circumscribed area of a to be monitored. After wiping the area, the sponge 5 is placed into a plastic bag 6 containing excess fluid and squeezed several times to release any of the absorbed bacteria into the collection fluid 3. The volume of collectate fluid can vary depending upon the size of the absorbent and area wiped. The collection fluid 3 is selected to ensure transfer of the microbial contaminants from the test surface to the collection device and then to a disposable test device. Generally the pH of the collection fluid 3 is between 5 and 8, but preferably between 6.0 and 7.0 and contains salts such as sodium chloride between 0.1M and 0.3M, preferably about 0.25M NaCl to ensure survival of bacteria. The collection fluid 3 should contain a detergent such as 0.05% Tween 20 to ensure that the bacteria are easily removed from the test surface and collection apparatus.

Figure 3:
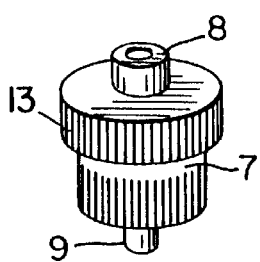
FIG. 3 is a frontal view of a large volume concentrating apparatus.
Figure 4:
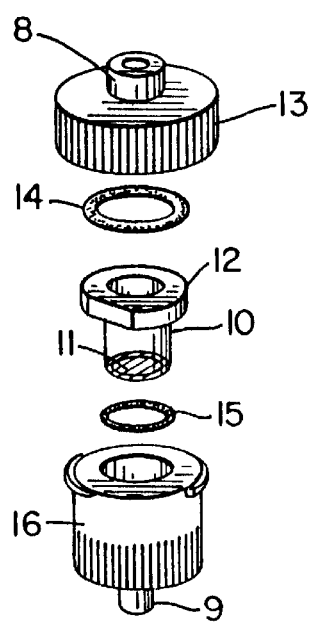
FIG. 4 is an exploded perspective view of a large volume concentrating apparatus.

Referring to FIGS. 3–4, a large volume concentrating apparatus 7 may be used in which a quantity of collectate fluid can be collected into a disposable test device. An appropriate sized Luer-tipped syringe is attached to the inlet 8 of large volume concentrating apparatus 7 and then positive pressure applied to the syringe plunger causing the collectate fluid to flow out of the outlet 9.

More specifically, the collectate fluid flows through the filter bottom 11 of the disposable test device 10. "O" rings 14 and 15 provides a leakproof seal. After completing the concentration of the collectate, upper compartment 13 is separated from the lower compartment 16 to expose the lip 12 of the disposable test device 10. The disposable test device is then manually removed from the lower compartment 16.

Figure 5:
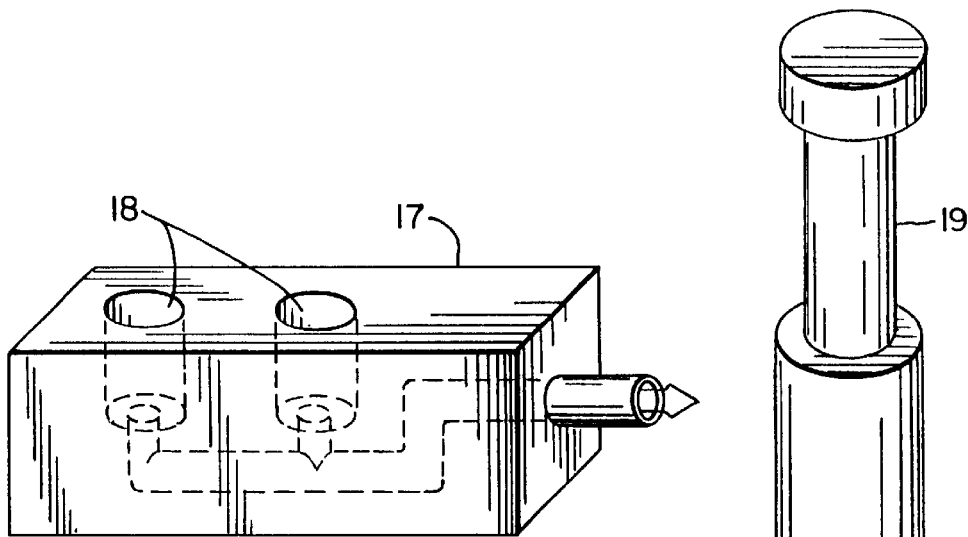
FIG. 5 is a cross-sectional side view of a negative pressure apparatus.
Figure 6:
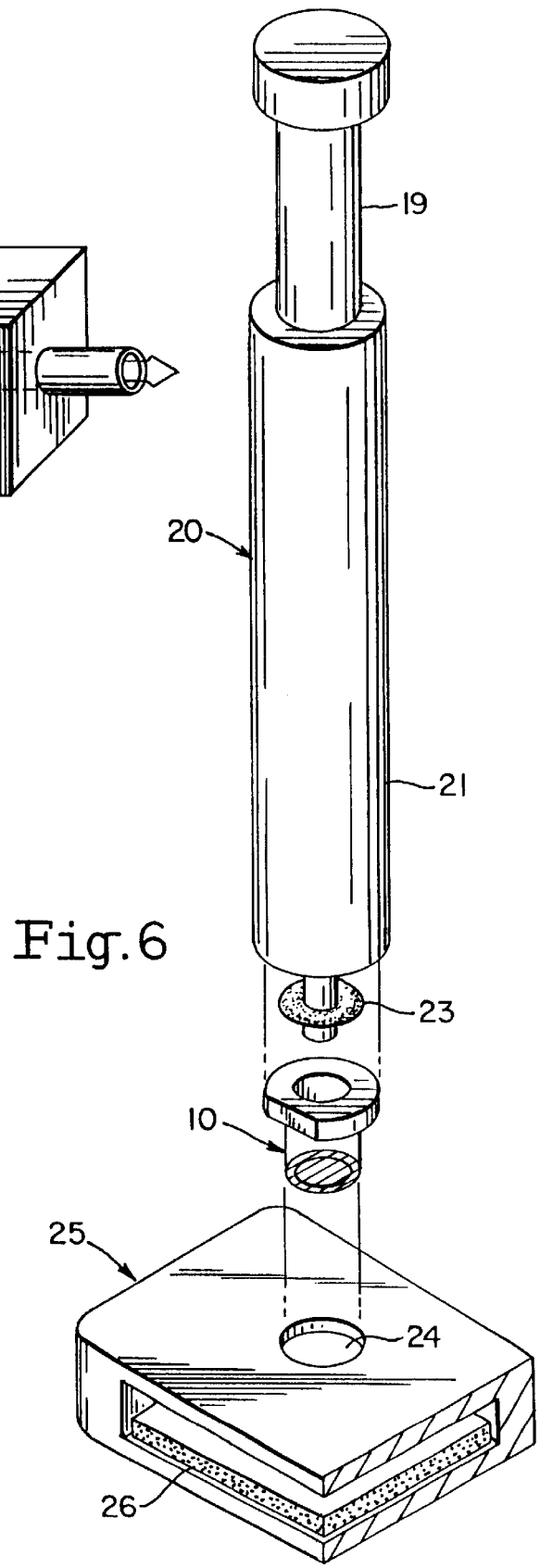
FIG. 6 is an exploded perspective drawing of a positive pressure apparatus, disposable test device and holder with absorbent disk.
Figure 7:
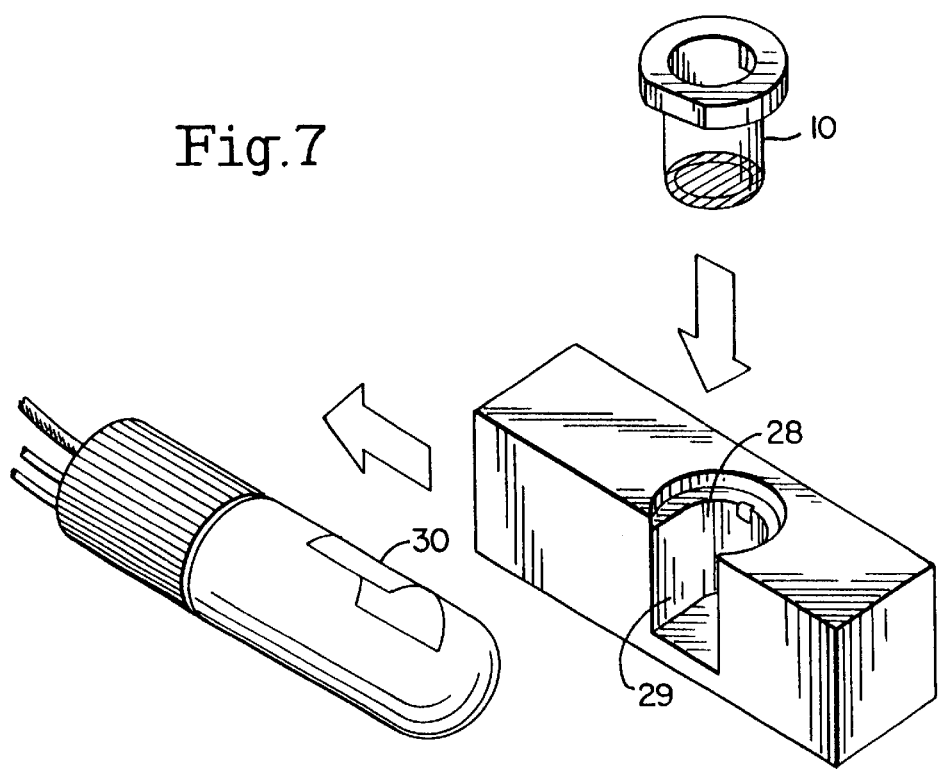
FIG. 7 is a drawing of the disposable test device, its respective positioning into the complementary draw slide and the relationship to the photosensor means.
Figure 8:
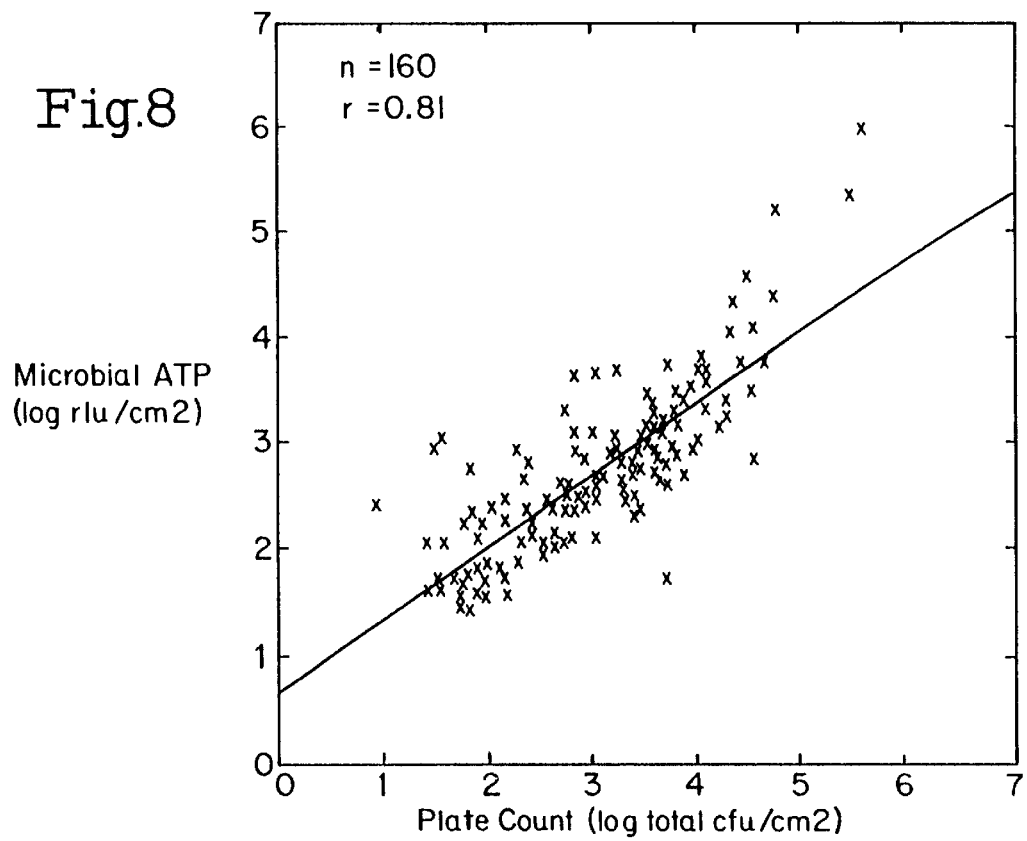
FIG. 8 is a graph of the total plate count obtained after 48 hours of incubation and the relative light units obtained from the 5 minute bioluminescent procedure outlined in the preferred embodiment with each data point representing a single beef carcass.
Figure 9:
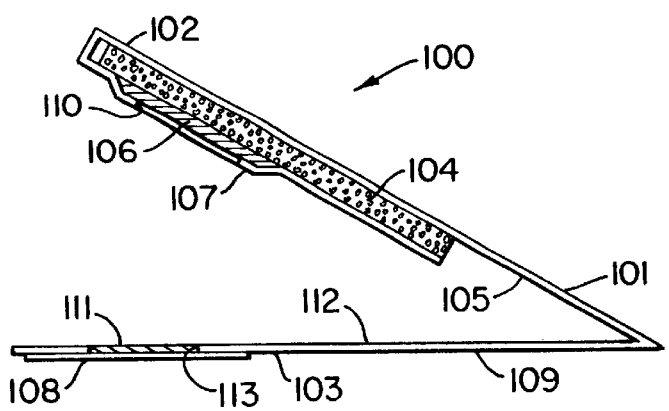
FIG. 9 is a cross section side view of the membrane ticket.
Figure 10:
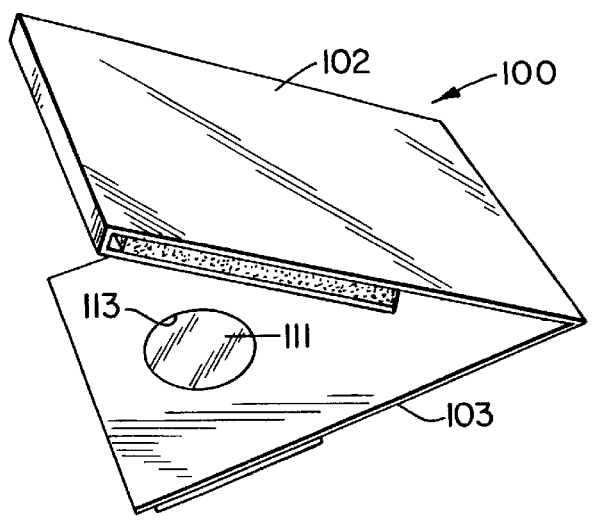
FIG. 10 is an angular overhead view of the membrane ticket.

Referring to FIGS. 5–7, a negative pressure device 17 in which the bottom portion of the disposable test device is inserted into holes 18. Appropriate volume of wash or somatic cell lysing solutions can be added and a vacuum can be applied to outlet 19 to remove fluid from the disposable test device 10. The somatic cell lysing step may be eliminated. In particular, when air and surface samples are tested, and even when standard water samples are tested, it has been found that the presence of somatic cells is rare.

A positive pressure apparatus 20 is comprised of a plunger 19 and a barrel 21, a disposable test device 10, and device holder 25 comprised of an absorbent pad or disk 26 to absorb the fluid waste. The disposable test device is inserted into holder 24. An aliquot of collectate fluid (i.e. 50 to 100 $\mu$l) is added and an appropriate volume of wash or somatic cell lysing solutions can be added. Once again, the step of lysing somnatic cell lysing may be eliminated. The rubber seal 23 of the positive pressure device is positioned on top of the disposable test device 10. Applying pressure to plunger 19 forces air through barrel 20 and out through outlet 22 displacing the fluid which passes into the absorbent disk 26. Additional wash solution can be added and the process repeated.

The disposable test device 10, is positioned 28 into the draw slide 27, where it can be read by photosensor means 30. The body of the disposable test device 10 is comprised of an optically clear molded plastic material, such as polystyrene, which is capable of nearly complete transmission of light within a 500–600 nm wavelength range. Fused to the lower surface of the device is a semi-permeable membrane 11 which is characterized by its strength and lack of deformation under pressure, and a pore size distribution which insures surface retention of bacterial cells, while facilitating complete passage of any associated liquid phase during pressurization. This membrane must also have sufficient surface tension to retain the measurement solution even after wetting.

The draw slide is an integral part of a luminometer instrument. The draw slide is pulled out and the disposable test device is positioned into hole 28 so that a window to the translucent wall of the disposable test device is exposed to the photosensor means when the draw slide is returned to a complementary dark chamber of the luminometer.

In a general bacterial screen based on bioluminescence, after a microbial sample has been concentrated in the disposable test device, at least one lytic enzyme produced by a bacteria infected with a bacteriophage specific for said bacteria is added to lyse a specific bacteria and free the ATP. An appropriate volume of luminescent substrate (i.e. luciferin-luciferase) is added to the disposable test device and the draw slide is returned to the dark chamber of the luminometer. Measurement of fight emission is made by digitalizing or converting the electrical signal from the photosensor means to a number of relative light units. If the method is to be used to detect specific bacteria, a specific antibody conjugated to a chemiluminescent or enzyme probe is added. In the preferred embodiment, the antibody is placed in the disposable test device and allowed to react for 10 minutes. Additional wash steps may be performed by adding a wash solution and evacuating the wash solution. A luminescent substrate solution is then added. In the preferred embodiment such substrate consists of a mixture of hydrogen peroxide and luminol. The draw slide is returned to the dark chamber of the luminometer. Measurement of light emission is made by digitalizing or converting the electrical signal from the photosensor means to a number of relative light units.

In another embodiment of the invention, all of the chemicals and solutions are in a disposable membrane ticket 100. As with the systems described above, all systems and procedures described below involve the detection and quantification of bacteria in samples which may also contain somatic cells, free ATP, and constituents such as chloride ions which are known to inhibit the luciferin-luciferase enzyme reaction. Again, it should be noted that in many substances to be tested, such as air, surfaces, water samples, etc., it would be rare to find somatic cells; hence, it is possible to eliminate the step of having a somatic cell releasing agent, as somatic cells would not be expected to be present in any significant amount.

The membrane ticket 100 preferably comprises a hinged two sided plastic, cardboard, or paper support 101 having a top section 102 and bottom section 103. An absorbent pad 104 is positioned on top of the inner side 105 of the top section 104. The absorbent pad 104 is comprised of a material made of cellulose. The material may be cotton, corn silk, possibly fiberglass, or other absorbent material. On top of absorbent disk 104 is a glass filter membrane 106, which may be held in place by a plastic or paper rigid layer 107.

The bottom section 103 of the membrane ticket 100 preferably comprises a transparent window 108 on the outer side 109 of the bottom section, and a luciferin-luciferase solution immobilized on the membrane disk 111. The membrane disk fits in a hole 113 in the bottom section 103 of the ticket 100.

To form the membrane ticket 100 with the luciferin-luciferase immobilized on the membrane, it is important to prepare a luciferin-luciferase buffer solution. One of many possible cocktails is described as follows: The buffer solution is comprised of 1% trehalose, 0.05M dithiothreitol (DTT), and 0.025M HEPES Buffer. The quantity required of each designated raw material in this cocktail is calculated by multiplying the quantity to be made by the required weight (g) or volume per ml. The following formulae may be followed:

$$\text{Trehalose} \underbrace{\qquad}_{\text{(Quantity to be made)}} ml \times .01 \ g/ml = \underbrace{\qquad}_{\text{(Quantity Required)}} g$$

$$\text{DTT} \underbrace{\qquad}_{\text{(Quantity to be made)}} ml \times .0078 \ g/ml = \underbrace{\qquad}_{\text{(Quantity Required)}} g$$

$$\text{HEPES} \underbrace{\qquad}_{\text{(Quantity to be made)}} ml \times .006 \ g/ml = \underbrace{\qquad}_{\text{(Quantity Required)}} g$$

The amount of water equivalent to 90% of the quantity of buffer solution to be made is determined by the formula:

$$\underbrace{\qquad}_{\substack{\text{(Quantity to} \\ \text{Made)}}} L \times .90 = \underbrace{\qquad}_{\substack{\text{(Amount of} \\ \text{Processed Water} \\ \text{Added)}}} L$$

The water is measured poured into a suitable container comprising a stirring bar. Each of the above mentioned buffer materials is added to the water and stirred until dissolution is complete. While continuing to stir, the ph of the solution is adjusted with 0.1 N NaOH to 7.8±0.01. An amount of processed water is added to the solution to bring the final volume to the desired amount. The luciferin Luciferase Spotting Reconstitution Buffer is passed through a 0.22μ membrane filter and, in a clean environment, collected in an autoclaved or other pre-sterilized screw cap container.

The required amount of luciferin-luciferase is then removed from the freezer and allowed to stand at room temperature for approximately 30 minutes. Working in a clean environment, the luciferin-luciferase is reconstituted in the Reconstitution Buffer 3.3 mol to a 5 ml. bottle or 10 ml for a 15 ml bottle of freeze dried material. The mixture is swirled gently, and allowed to equilibrate for approximately one hour. The reconstituted luciferin luciferase is filtered through a sterile 0.2μ syringe filter into sterile 12×75 tubes. The tip of a micropipette is dipped into methanol and the chamber of the micropipette is filled with Methanol. The methanol is expelled into a waste container and the chamber is rinsed with processed water in the same manner several times. The micropipette is filled with the luciferin-luciferase solution a number of times, preferably four, to clear the tip, and the pipetted solution is dispensed.

Each absorbent membrane or membrane disk 111 is then spotted with 101 μl of luciferin luciferase buffer until the desired number of disks have been spotted.

The spotted membrane disks 111, having been spotted in a suitable container, are then placed, while still in the container, into a −40° C. freezer for at least 45 minutes. The disks are then removed from the freezer and are lyophilized overnight (or for about at least 8 hours). The membrane disks 111 may be lyophilized while still in the containers, or removed from the containers during lyophilization. Once the spotted membrane disks 111 have been lyophilized, the containers containing the membrane disks 111 are stored in a container filled with desiccant. The membrane disks 111 should be stored in a refrigerator, being kept at about 4° C.

In another embodiment of the invention, somatic or cell releasing agent or at least one lytic enzyme produced by a bacteria infected with a bacteriophage specific for said bacteria may be incorporated into the glass membrane 106 in much the same manner as the luciferin-luciferase solution is incorporated in to the membrane disk 111. In a preferred embodiment of the invention, a somatic releasing agent may or may not be used and incorporated into the class membrane 106. However, the lytic enzyme is preferably immobilized on the membrane disk. The lytic enzyme may be lyophilized onto the membrane disk 111.

In assembling the ticket membrane 100 the assembler should take steps to avoid contamination of the membrane and the disks. Similarly, all work should be conducted in a clean environment.

The clean folded membrane tickets 100, are with the exception of the transparent window 108, manufactured by conventional means.

In a clean environment, and incorporating an adhesive tape to the bottom side of the plastic ticket, the membrane disk 111 is applied to the ticket 100 such that the membrane disk 111 is centered on the hole 113.

To use the membrane ticket 100, a sample volume of 25 μl, collected by normal means, is applied through a hole 110 in the rigid layer 107 onto the surface of the glass filter membrane 106. The glass filter membrane 106 retains bacterial and somatic cells on the surface of the glass filter membrane 106 while fluids pass into the absorbent disk 104.

If not already incorporated, somatic cell releasing agent is then added onto the surface of the glass filter membrane 106. The somatic cell releasing agent is added dropwise onto the surface of the glass membrane 106 so as to avoid flooding the membrane ticket and washing the cells out of the glass filter membrane 106. In another embodiment of the invention, no somatic cell releasing agent is used at all.

After the addition of the somatic cell releasing agent, the somatic cells have lysed and the released ATP from the somatic cells, along with free ATP and inhibitory materials which could have contaminated the results, are trapped in the absorbent pad. At this stage only bacterial cells are left intact on the surface of the glass filter membrane disk 106. In another alternative approach, somatic releasing reagent may be placed onto the swab used to streak the surface area being tested, thereby breaking the cells and releasing the ATP at that point.

Next, 10 μl or less of the lytic enzyme are applied, to the glass filter membrane 106, or preferably to the surface of a membrane 111 positioned on the inner side 112 of the bottom section 103 of the membrane ticket 100. As noted above, in a preferred embodiment, the lytic enzyme may already be incorporated into or onto the membrane disk 111. The luciferin-luciferase may be either saturated throughout the membrane 111, or found at the surface of the membrane 111.

The top section 102 and bottom section of 103 of the membrane ticket 100 are then compressed together, preferably upon the insertion of the disposable membrane ticket into the draw slide of the luminometer, and as the draw slide of the luminometer is pushed into the luminometer. As the top section 102 and bottom section 103 of the membrane ticket 100 make contact, the light producing reaction:

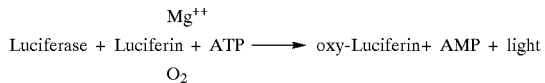

is initiated.

This results in RLU's over a ten second integration period, which corresponds with the bacterial content of the sample.

Figure 11:
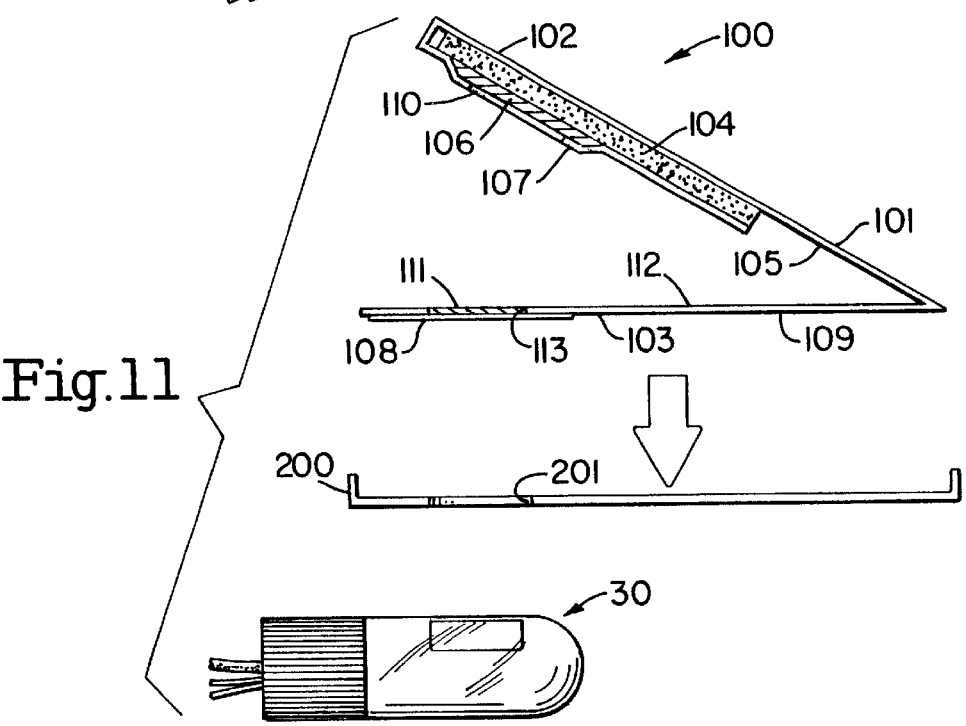
FIG. 11 is a cross-sectional view of the membrane ticket positioned over the photomultiplier.

As shown in FIG. 11, the membrane ticket 100 is preferably placed in the draw slide 200 of the luminometer with the luciferin-luciferase membrane face down, directly over a reading hole 201. The photomultiplier tube 30 is positioned directly under the hole 201.

This method may be used not just for the testing of surfaces, but also for the testing of fluids of all kinds, including air and liquids, and powders. This method may also be used to test for bacteria in food processing factories. Culture confirmations may be performed using these procedures.

Additionally, while the presence of lysed bacteria may be detected by the use of a luminometer, the steps described above can also be used to detect the bacteria by a variety of immunological and chromatographical techniques, once the sample has been purified and the target bacterial cells are lysed.

It should be noted that there may be a low level of luminescence given off by the reaction of ATP from unlysed cells with the luciferin-luciferase. However, the greatest ATP luminescence reaction will be from the lysed bacterial cells. The luminometer can be adjusted to compensate for any- "background" illumination.

Many different bacteria may be detected using this method, including but not limited to Salmonella, *E. coli*, Lysteria, *Streptococcus pneumoniae, Streptococcus fasciae, Staphylococcus aurea*, and many others.

The use of a lytic enzyme for the detection and count of bacteria is not limited to the use of the enzyme on a membrane ticket. The lytic enzyme may also be used in flourescent detection system, a reflective detection system, for rupturing cells to assay a bacteria by studying the constituents of the bacteria, or for any other number of detection systems. This enzyme may be used to detect and quantify bacteria using other illuminescent systems and methods, wherein the rupturing of the cell is necessary or helpful to detect and quantify some quality of the cell including but not limited to conductance, reflectance, and other systems. Indeed the lytic enzyme may also be utilized with various detection systems in addition to photomultiplier tube systems including photodiode, charge coupled devices, photographic imaging, visual luminescence, lateral flow gold immunoassay systems, and others.

For example, the lytic enzyme may be used to lyse the bacteria to study the mitochondria of the cell. The lytic enzyme may also be used to lyse cells to help determine the radioactive count where radioactive markers have been added to the cells via the growth media. Fluorescent techniques may also be used to quantify the bacteria after the bacteria have been lysed. Reflectance systems can be used in conjunction with the lytic enzyme technology. The use of this (these) lytic enzyme(s) may be used with various immunological assays, wherein the antibodies are directed against various internal components of the bacteria, such that the lysing of the cell yields superior immunological responses. The rupturing of specific bacterial cells to expose cell fragments enhances the accuracy of detection. These techniques, which can include lateral flow, flow through, agglutination, and other similar tests used in immunological studies, may be used to identify the bacteria. The lytic enzymes may also be used for the colorimetric assay or identification of bacteria or constituents thereof The lytic enzyme may also be used in visual tests, wherein the enzyme is added to an aliquot of a turbid sample. If the phage associated lytic enzyme is specific for the contaminating bacteria, there will be a visual change of the sample.

Indeed, lytic enzymes may be used in place of bacterial releasing agent so as to lyse specific bacteria for any and all kinds of bacterial detection and quantification systems. More than one lytic enzyme may be used where the precise determination of the bacteria present is not as critical, or when it is desirable to assay for more than one particular bacteria.

The following example illustrates the use of the lytic enzyme for the use of the enzyme in an ATP detection assay.

Phage Associated Enzyme / ATP Detection Assay

The releasing reagent containing the group C phage lysin enzyme is prepared as follows:

Group C streptococcal strain 26RP66 (ATCC #21597) or any other group C streptococcal S strain is grown in Todd Hewitt medium at 37 degree. C. to an OD of 0.23 at 650 nm in an 18 mm tube. Group C bacteriophage (C1) (ATCC #21597-B1) at a titer of 5.times.10.sup. 6 is added at a ratio of 1 part phage to 4 parts cells. The mixture is allowed to remain at 37 degree. C. for 18 min at which time the infected cells are poured over ice cubes to reduce the temperature of the solution to below 15 degree. C. The infected cells are then harvested in a refrigerated centrifuge and suspended in 1/300th of the original volume in 0.1M phosphate buffer, pH 6.1 containing 5.times.10.sup.−3M dithiothreitol and 10 ug of DNAase. The cells will lyse releasing phage and the lysin enzyme. After centrifugation at 100,000.times. g for 5 hrs to remove most of the cell debris and phage, the enzyme solution is aliquoted and tested for its ability to lyse Group A Streptococci.

The number of units/ml in a lot of enzyme is determined to be the reciprocal of the highest dilution of enzyme required to reduce the OD650 of a suspension of group A streptococci at an OD of 0.3 to 0.15 in 15 min units are produced in a single 12 liter batch.

Use of the enzyme in an immunodiagnostic assay requires a minimum number of units of lysin enzyme per test depending on the incubation times required. The enzyme is diluted in a stabilizing buffer containing the appropriate conditions for stability, maximum enzymatic activity, inhibitors of nonspecific reactions, and in some configurations contains specific antibodies to the Group A carbohydrate. The preferred embodiment is to use a lyophilized reagent which can be reconstituted with water. The stabilizing buffer can comprise a reducing reagent, which can be dithiothreitol in a concentration from 0.001M to 1.0M, preferably 0.005M. The stabilizing buffer can comprise an imrnunoglobulin or immunoglobulin fragments in a concentration of 0.001 percent to 10 percent, preferably 0.1 percent. The stabilizing buffer can comprise a citrate-phosphate buffer in a concentration from 0.001M to 1.0M, preferably 0.05M. The stabilizing buffer can have a pH value in the range from 5.0 to 9.0. The stabilizing buffer can comprise a bactericidal or bacteriostatic reagent as a preservative. Such preservative can be sodium azide in a concentration from 0.001 percent to 0.1 percent, preferably 0.02 percent.

The preparation of phage stocks for lysin production is the same procedure described above for the infection of phage and group C streptococcus in the preparation of the lysin enzyme. However, instead of pouring the infected cells over ice, the incubation at 37 degree. C. is continued for a total of 1 hour to allow lysis and release of the phage and also enzyme in the total volume. In order for the phage to be used for subsequent lysin production the residual enzyme must be inactivated or removed to prevent lysis from without of the group C cells rather than phage infection.

Bacteria, Group A Streptococci (GAS: ATCC #12385), and Group B Streptococci (GBS: ATCC #13813), were streaked from frozen stocks onto tryptic soy agar plates and incubated for 18 hours at 37° C. Bacterial colonies were harvested into sterile 0.9% NaCl. The optical density (OD) of the solution was measured at 650 nm and the concentration adjusted so the OD was 0.300 by diluting the bacteria in 0.05M Tris, 0.05M EDTA, 0.15 NaCl at pH 8.2. 100 µl of the sample was added to a disposable test device. 100 µl of wash solution (SRA) comprising 0.05% saponin in 0.1M Hepes buffer, pH 7.75 was added. Using a positive pressure device, the fluidphase in the disposable test device was passed through the membrane onto a pad of paper towels. An additional 150 µl of SRA wash solution was added and using the positive pressure device, was passed through the membrane of the device onto a pad of paper towels. The disposable test device was placed into the drawslide of a luminometer and 50 µl of bacterial releasing reagent (BRA), consisting of 100 units/mL of the Phage Associated Enzyme (PAE) prepared above in Glycerol buffer. The solution was incubated for 0, 2, 5 minutes, after which time 50 µl of Luciferin/Luciferase/magnesium solution was added. The draw slide of the luminometer was closed and the light emission was read. The entire procedure required under 5 minutes to perform per sample. The results were expressed in relative light units (RLU).

| Sample | Incubation | RLU |
|---|---|---|
| GAS | 0 min | 49 |
| GAS | 2 min | 119 |
| GAS | 5 min | 432 |
| GBS | 0 min | 17 |
| GBS | 2 min | 20 |
| GBS | 5 min | 21 |

The samples were also tested utilizing the same procedure, except substituting 50 µl of bacterial releasing agent (BRA) consisting of 0.1M benzyl Sodium Chloride in Hepes buffer, pH 7.75 followed by the addition of 50 µl of Luciferin/Luciferase/Magnesium (L/L/m) solution. The drawslide of the luminometer was closed and light emission was read. Results are noted below.

Group A Strep+SRA+BRA→580 RLU

Group B Strep+SRA+BRA→174 RLU

The Phage Associated Enzyme (PAE) was further tested without the presence of any sample. Total PAE was added to the test device. 50 µl of PAE was added to the test device. 50 µl of L/L solution was added. The drawslide of the luminometer was closed and light emission was read.

PAE+L/L→17RLU

These tests demonstrate the Phage Associated Enzyme could, with a 5 minute incubation, through selective lysing of cells, identify specific Group A Strep bacteria utilizing detection of ATP with a luminometer. The same enzyme, when applied to a Group B Streptococci sample, yielded a result, comparable to a background testing.

Incubation of the sample with 50 µl PAE for 5 min. effectively lyses GAS organisms with the resulting release of ATP, without rupturing significant numbers of GBS cells.

Many modifications and variations of the present invention are possible in light of the above teachings. It is, therefore, to be understood within the scope of the appended claims the invention may be protected otherwise than as specifically described.

What is claimed is:

1. A method for using a lytic enzyme to determine the presence and quantity of a specific bacteria in a sample, comprising:

a) collecting a liquid sample;

b) placing said liquid sample on a disposable test device with at least one permeable filter, said disposable test device being a membrane ticket, said membrane ticket comprising:

a hinged two side support having a top section and a bottom section, an absorbent pad positioned on top of an inner side of said top section, a filter membrane, on top of said absorbent pad, a rigid layer holding said at least one filter membrane in place;

a rigid layer positioned over said at least one filter membrane;

a hole in said rigid layer positioned over said at least one filter membrane;

a hole in the bottom section of the membrane ticket;

a membrane disk fitted in said hole of said membrane ticket;

an illumination solution immobilized on said membrane disk;

a transparent window on an outer side of said bottom section under said membrane disk;

wherein said sample is applied through said hole in the rigid layer onto the surface of the filter membrane, when said membrane ticket is in an open position;

c) applying at least one lytic enzyme produced by a bacteria infected with a bacteriophage specific for the bacteria that lyses said specific bacterial cells to the surface of the membrane disk positioned on the inner side of the bottom section of the membrane ticket;

d) compressing the top section and bottom section of the membrane ticket;

e) sliding the membrane ticket in a photometer by means of a draw slide; and f) measuring the light emission resulting from said luminescent reaction with a photometer comprising a photodetector system and a light tight chamber for said disposable test device and device to measure light passing through said transparent wall of said membrane ticket; and g) causing said photodetector means to output a signal indicative of the presence and amount of said specific bacteria in said sample.

2. The method according to claim 1 wherein steps (c) through (g) are performed within about one hour.

3. The method according to claim 2, wherein steps (c) through (g) are performed within about 30 minutes.

4. The method according to claim 1 wherein said disposable collection apparatus means is comprised of a soft absorbent.

5. The method according to claim 1 wherein said disposable collection apparatus means consists of a spongy absorbent.

6. The method according to claim 1 wherein said disposable collection apparatus means is comprised of a soft absorbent and a shaft.

7. The method according to claim 1 wherein said collection fluid contains a detergent.

8. The method according to claim 1 wherein said collection fluid contains a salt.

9. The method according to claim 1 wherein said analyte contains adenosine triphosphate (ATP) and said light emission correlates with the concentration of said ATP.

10. The method according to claim 1 in which a large volume concentrating apparatus is used to concentrate the fluid in said disposable test device as part of step (c).

11. The method according to claim 1 in which said filter means is a hydrophilic permeable membrane.

12. The method according to claim 1 in which all light emitting substances are retained within disposable test device during the performance of step (f).

13. The method according to claim 1, wherein said membrane ticket is comprised of a material selected from the group consisting of plastic, cardboard, or paper.

14. The method according to claim 1, wherein said absorbent pad is comprised of cellulose.

15. The method according to claim 1, wherein said absorbent pad is selected from the group consisting of cotton, corn silk, and fiberglass.

16. The method according to claim 1, wherein said filter membrane is comprised of a glass filter.

17. The method according to claim 1, wherein said illumination solution is a luciferin-luciferase solution.

18. The method according to claim 17, wherein said luciferin-luciferase solution comprises luciferin, luciferase, and magnesium.

19. The method according to claim 18, wherein said luciferin-luciferase solution further comprises the chemicals selected from the group consisting of trehalose, dithiothreitol, HEPES buffer, and combinations thereof.

20. The method according to claim 1, wherein said photodetector means is positioned directly under the membrane disk, said membrane disk being face down over said luminometer.

21. The method according to claim 1, wherein said method further comprises adding a somatic cell releasing agent through said hole in said rigid layer onto the surface onto the surface of said filter membrane after said sample has been added when said membrane ticket is still in an open position.

22. The method according to claim 1, wherein said membrane ticket further comprises a somatic cell releasing agent incorporated on the surface of the filter membrane.

23. The method according to claim 22, wherein said somatic cell releasing agent is lyophilized on the surface of the filter membrane, prior to use of said membrane ticket.

24. A method for using a lytic enzyme to determine the presence and quantity of a specific bacteria in a sample of anayte comprising:

a) collecting a liquid sample of said analyte;

b) placing said liquid sample on a disposable test device with at least one permeable filter, said disposable test device being a membrane ticket, said membrane ticket comprising:

a hinged two side support having a top section and a bottom section, an absorbent pad positioned on top of an inner side of said top section, a filter membrane, on top of said absorbent pad, a rigid layer holding said filter membrane in place;

a hole in said rigid layer positioned over said filter membrane;

a hole in the bottom section of the membrane ticket;

a membrane disk fitted in said hole of said membrane ticket;

a lytic enzyme produced by a bacteria infected with a bacteriophage specific for said bacteria, said lytic enzyme immobilized on said membrane disk;

an illumination solution immobilized on said membrane disk;

a transparent window on an outer side of said bottom section under said membrane disk;

wherein said sample is applied through a hole in the rigid layer onto the surface of the filter membrane;

d) compressing the top section and bottom section of the membrane ticket;

e) sliding the membrane ticket in a photometer by means of a draw slide;

f) measuring the light emission resulting from said luminescent reaction with a photometer comprising a photodetector means and a light tight chamber for said disposable test device and a means to measure light passing through said transparent wall of said membrane ticket; and g) causing said photometer means to output a signal indicative of the presence and amount of analyte.

25. The method of claim 24, wherein said lytic enzyme is lyophilized on said membrane disk prior to use of said membrane ticket.

26. The method of claim 24, wherein said lytic enzyme is dried onto said membrane disk prior to use of said membrane ticket.

27. The method according to claim 24, wherein said method further comprises adding a somatic cell releasing agent through said hole in said rigid layer onto the surface onto the surface of said filter membrane after said sample has been added when said membrane ticket is still in an open position.

28. The method according to claim 24, wherein said membrane ticket further comprises a somatic cell releasing agent incorporated on the surface of the filter membrane.

29. The method according to claim 28, wherein said somatic cell releasing agent is lyophilized on the surface of the filter membrane, prior to use of said membrane ticket.

30. A membrane ticket for placing in a luminometer a sample for obtaining a bacterial count, said membrane ticket comprising:

a hinged two side support having a top section and a bottom section, an absorbent pad positioned on top of an inner side of said top section, at least one filter membrane, on top of said absorbent pad, a rigid layer holding said filter membrane in place;

a rigid layer positioned over the filter membrane;

a hole in said rigid layer positioned over said filter membrane;

at least one lytic enzyme produced by a bacteria infected with a bacteriophage specific for the bacteria; incorporated in the surface of the filter membrane;.

a hole in the bottom section of the membrane ticket;

a membrane disk fitted in said hole of said membrane ticket;

an illumination solution immobilized on said membrane disk; and a transparent window on an outer side of said bottom section under said membrane disk;

wherein said sample is applied through a hole in the rigid layer onto the surface of the filter membrane.

31. The membrane ticket according to claim 30, wherein said membrane ticket further comprises a somatic cell releasing agent incorporated on the surface of the membrane filter.

32. The membrane ticket according to claim 31, wherein said somatic cell releasing agent is lyophilized on the surface of the filter membrane, prior to use of said membrane.

33. A method for using at least one lytic enzyme to determine the presence and quantity of a specific bacteria in a sample, comprising:

exposing said bacteria to said lytic enzyme, wherein if said at least one lytic enzyme produced by a bacteria infected with a bacteriophage specific for the bacteria, said bacteria lyse; and quantifying said bacteria after said bacteria are lysed by said at least one lytic enzyme.

34. The method according to claim 33, wherein said bacteria are quantified by the use of a luminometer.

35. The method according to claim 33, wherein said bacteria are quantified by the use of fluorescence.

36. A method for using at least one lytic enzyme to determine the presence of a specific bacteria in a sample, comprising:

exposing said bacteria to said lytic enzyme, wherein if said at least one lytic enzyme produced by a bacteria infected with a bacteriophage specific for the bacteria, said bacteria lyse; and identifying said bacteria after said bacteria are lysed by said at least one lytic enzyme.

37. The method according to claim 33, wherein said bacteria are identified by use of a luminometer.

38. The method according to claim 33, wherein said bacteria are identified by use of fluorescence.

* * * * *